United States Patent
Paoli, Jr.

(10) Patent No.: US 7,981,097 B2
(45) Date of Patent: Jul. 19, 2011

(54) MEDICAL DEVICE FOR THE TREATMENT AND PREVENTION OF EYE AND RESPIRATORY TRACT CONDITIONS

(76) Inventor: Alexander Delli Paoli, Jr., Libertyville, IL (US)

( * ) Notice: Subject to any disclaimer, the term of this patent is extended or adjusted under 35 U.S.C. 154(b) by 618 days.

(21) Appl. No.: 12/056,757

(22) Filed: Mar. 27, 2008

(65) Prior Publication Data

US 2009/0247967 A1    Oct. 1, 2009

(51) Int. Cl.
*A61F 13/02*    (2006.01)
(52) U.S. Cl. .......................................... 604/298; 604/294
(58) Field of Classification Search .......... 604/294–296, 604/298, 300–303; 351/65, 78, 80, 136, 351/138
See application file for complete search history.

(56) References Cited

U.S. PATENT DOCUMENTS

| | | | |
|---|---|---|---|
| 4,336,799 A | 6/1982 | Almasi et al. | |
| 4,405,212 A | 9/1983 | Cooper | |
| 5,193,534 A * | 3/1993 | Peppler | 128/207.18 |
| 5,229,128 A | 7/1993 | Haddad et al. | |
| 5,368,582 A * | 11/1994 | Bertera | 604/295 |
| 5,467,147 A | 11/1995 | Faranda | |
| 5,588,564 A | 12/1996 | Hutson et al. | |
| 5,636,787 A | 6/1997 | Gowhari | |
| 5,794,635 A | 8/1998 | Maines | |
| 5,807,357 A | 9/1998 | Kang | |
| 5,878,742 A | 3/1999 | Figueredo et al. | |
| 5,966,680 A | 10/1999 | Butnaru | |
| 6,139,144 A | 10/2000 | Hynansky | |
| 6,230,046 B1 | 5/2001 | Crane et al. | |
| 6,270,467 B1 | 8/2001 | Yee | |
| 6,312,393 B1 | 11/2001 | Abreu | |
| 6,312,403 B1 | 11/2001 | Ruiz | |
| 6,350,275 B1 | 2/2002 | Vreman et al. | |
| 6,511,175 B2 | 1/2003 | Hay et al. | |
| 6,824,265 B1 | 11/2004 | Harper | |
| 6,851,626 B2 | 2/2005 | Patel et al. | |
| 6,994,433 B2 | 2/2006 | Hockaday et al. | |
| 7,036,927 B2 | 5/2006 | Kopfer | |
| 7,077,137 B2 * | 7/2006 | Russell | 128/206.12 |
| 7,114,807 B2 | 10/2006 | Tagawa | |
| 7,231,922 B2 | 6/2007 | Davison et al. | |
| 7,300,151 B2 | 11/2007 | Yee | |
| 2002/0124843 A1 | 9/2002 | Skiba et al. | |
| 2003/0081169 A1 | 5/2003 | Kopfer | |
| 2005/0240162 A1 | 10/2005 | Chen et al. | |

(Continued)

FOREIGN PATENT DOCUMENTS

GB    2 409 166    6/2005

(Continued)

*Primary Examiner* — Melanie J Hand
(74) *Attorney, Agent, or Firm* — Dykema Gossett PLLC (57) ABSTRACT

A medical device for the treatment and prevention of eye and respiratory tract conditions is provided. The medical device may include a pack with a pump, a filter, and a vaporizer chamber for storing fluid and selectively supplying fluid vapor to ambient air. The medical device may further include a glasses unit comprising a pair of frames and a diffuser. The medical device may further include a tube having a first end configured for connection to the pack and a second end configured for connection to the diffuser. The glasses unit may be separated from the pack when the medical device is in use. Various methods for the treatment and prevention of eye and respiratory tract conditions and a method for modifying a pair of conventional glasses for treatment are also disclosed.

17 Claims, 10 Drawing Sheets

U.S. PATENT DOCUMENTS

| | | |
|---|---|---|
| 2006/0289009 A1 | 12/2006 | Palomo et al. |
| 2007/0068514 A1 | 3/2007 | Giroux |
| 2007/0131230 A1 | 6/2007 | Giroux |
| 2007/0265505 A1* | 11/2007 | Guillon et al. ............... 600/300 |
| 2007/0277829 A1 | 12/2007 | Casewell |

FOREIGN PATENT DOCUMENTS

| | | |
|---|---|---|
| JP | 168573 | 6/1997 |
| WO | WO 99/36014 | 7/1999 |
| WO | WO 2005/058151 A1 | 6/2005 |

* cited by examiner

FIG. 1
FLOW SHEET

FIG. 3

ADAPTED COMMERCIAL GLASSES

FIG. 4
SPECIALTY MEDICAL FRAMES WITH DIFFUSERS

FIG. 5

ADAPTED COMMERCIAL GLASSES

FIG. 6

SPECIALTY MEDICAL FRAMES WITH DIFFUSERS

FIG. 7

SPECIALTY MEDICAL FRAMES WITH CANNULAS

FIG. 8
SPECIALTY MEDICAL FRAMES WITH MASK

FIG. 9
MEDICAL DEVICE GENERAL VIEW

FIG. 10

SPECIALTY MEDICAL FRAMES
WITH MEDICAL GAS SOURCE

MEDICAL DEVICE FOR THE TREATMENT AND PREVENTION OF EYE AND RESPIRATORY TRACT CONDITIONS

BACKGROUND OF THE INVENTION a. Field of the Invention

The instant invention relates to a medical device for the treatment and prevention of eye and respiratory tract conditions. In one embodiment, the medical device may be portable.

b. Background Art

Many conditions of the eyes and respiratory tract may be offered relief by introducing treatment over extended time. These conditions include: dry eyes, environmental irritants, allergies from the environment, and various drug treatments best delivered by vaporization and/or sustained contact of the eyes and respiratory tract.

Previous attempts to treat the eyes have included bulky and conspicuous goggle units that fully enclose the eye chamber. Bulky goggle units increase the size and weight of the treatment device, making the device less portable. Furthermore, conspicuous goggle units may discourage use of the treatment device in public, thereby effectively limiting its use to only private areas. It may be desirable to make a medical device for the treatment and prevention of eye and respiratory tract conditions that is lighter and less bulky in an effort to improve portability. It may also be desirable to make a medical device for the treatment and prevention of eye and respiratory tract conditions that is less conspicuous, so that recipients of the treatment may use the medical device in public without standing out and may even be able to utilize conventional glasses or other spectacle-like frames for glasses.

Previous attempts to treat the eyes have also included the use of nebulizers to reduce a solution into a fine spray or mist. The spray or mist may be carried by currents of air toward the eye chamber. The use of nebulizers is problematic because nebulizers produce liquid droplets in mist or spray form that are carried by air streams. If liquid droplets are included in the air stream at the time of delivery, visibility of the glasses may be reduced because of excessive liquid and condensation. It may be desirable to make a medical device for the treatment and prevention of eye and respiratory tract conditions that avoids delivery of liquid droplets at the time of release/delivery of the air stream to the eyes or respiratory tract.

It may be desirable to provide a novel therapeutic platform for providing filtration, supplying vapor and/or humidity, and delivering various drug treatments depending upon the treatment protocol or regimen recommended by medical personnel.

BRIEF SUMMARY OF THE INVENTION

A medical device for the treatment and prevention of eye and respiratory tract conditions is provided. The medical device may include a pack with a pump for drawing in ambient air, a filter for filtering air drawn in by the pump, and a vaporizer chamber for storing fluid and selectively supplying fluid vapor to air drawn in by the pump. The medical device may further include a glasses unit for fitting over both of the eyes of a user. The glasses unit may comprise a pair of spectacle-like frames and a diffuser connected to the frames. The diffuser may be configured to deliver air drawn in from the pump, wherein the air does not include liquid at the time of delivery. The medical device may further include a tube having a first end and a second end. The first end of the tube may be configured for connection to the pack, and the second end of the tube may be configured for connection to the diffuser. The glasses unit may be separated from the pack when the medical device is in use.

Various methods of treating eye and respiratory tract conditions are also disclosed. The method of treating eye and respiratory tract conditions may include the step of providing a medical device including a pack and a glasses unit. The pack may include a pump, a filter, and a vaporizer chamber, and the glasses unit may include spectacle-like frames and a diffuser. The medical device may further include a tube having a first end configured for connection to the pack and a second end configured for connection to the diffuser. The method may further include the steps of filtering air drawn in from the pump and delivering the filtered air to the eye area of the user. The filtered air may not include liquid at the time of delivery. The method may further include the steps of supplying vapor to the air drawn in from the pump and delivering the air to the eye area of the user.

Another method may further include the steps of removing the diffuser from the frames, inserting a block configured to plug the frames in place of the diffuser, connecting a cannula to the medical device, and delivering the filtered air to the cannula. Another method may further include the steps of connecting a mask to the medical device, the mask configured to form an enclosure around the nose area of the user of the device, and delivering the filtered air to the enclosure. These methods may further include the steps of supplying vapor to the air drawn in from the pump and delivering the air to the cannula or to the enclosure formed by the face mask.

Methods may further include the steps of introducing a medication into the vaporizer chamber and delivering the medication by vaporization to the eye area of the user, to the cannula, or to the enclosure formed by the face mask.

Another method of treating eye and respiratory tract conditions may include the step of providing a medical device including a glasses unit and a tube. The glasses unit may be configured to fit over both of the eyes of a user and may include spectacle-like frames, a diffuser, and a cannula. The tube of the medical device may have a first end configured for connection to the glasses unit. The second end of the tube of the medical device may be configured for connection to a container for medical gas. The method may include the steps of connecting the second end of the tube to the container for medical gas and delivering the medical gas to the glasses unit.

A method of modifying a pair of glasses is also disclosed. The method may include the step of providing a pack including a pump, a filter, and a vaporizer chamber. The method may further include the step of providing a tube having a first end configured for connection to the pack and a second end configured for connection to a diffuser for delivering air drawn in from said pump. The method may further include the step of connecting the tube to the glasses.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
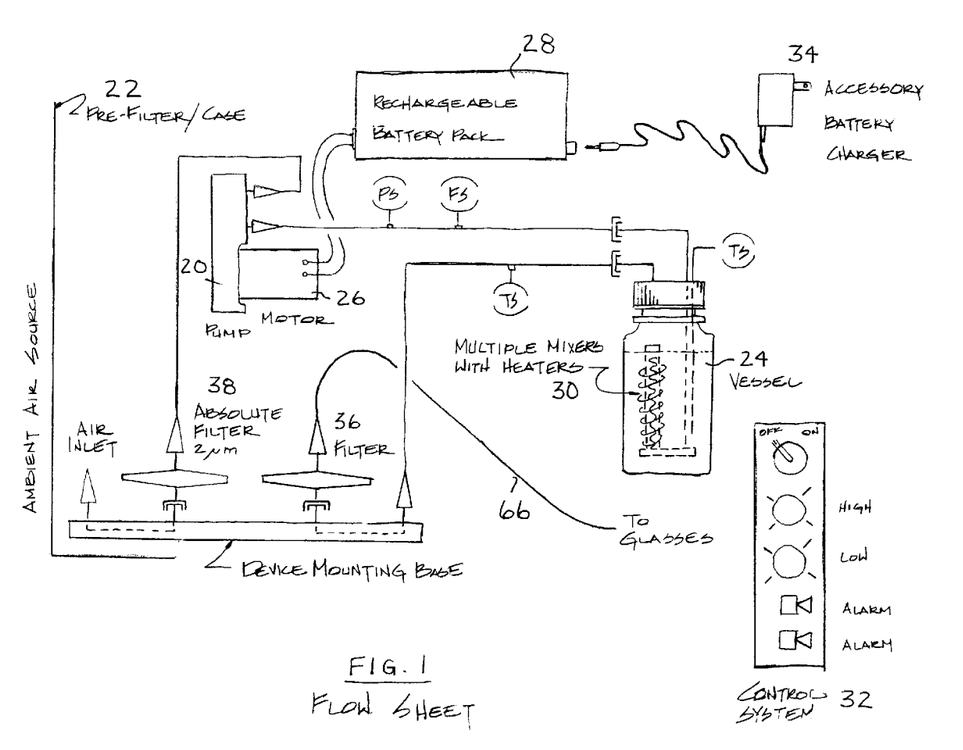
FIG. 1 is a flow chart for a medical device in accordance with an embodiment of the invention.
Figure 8:
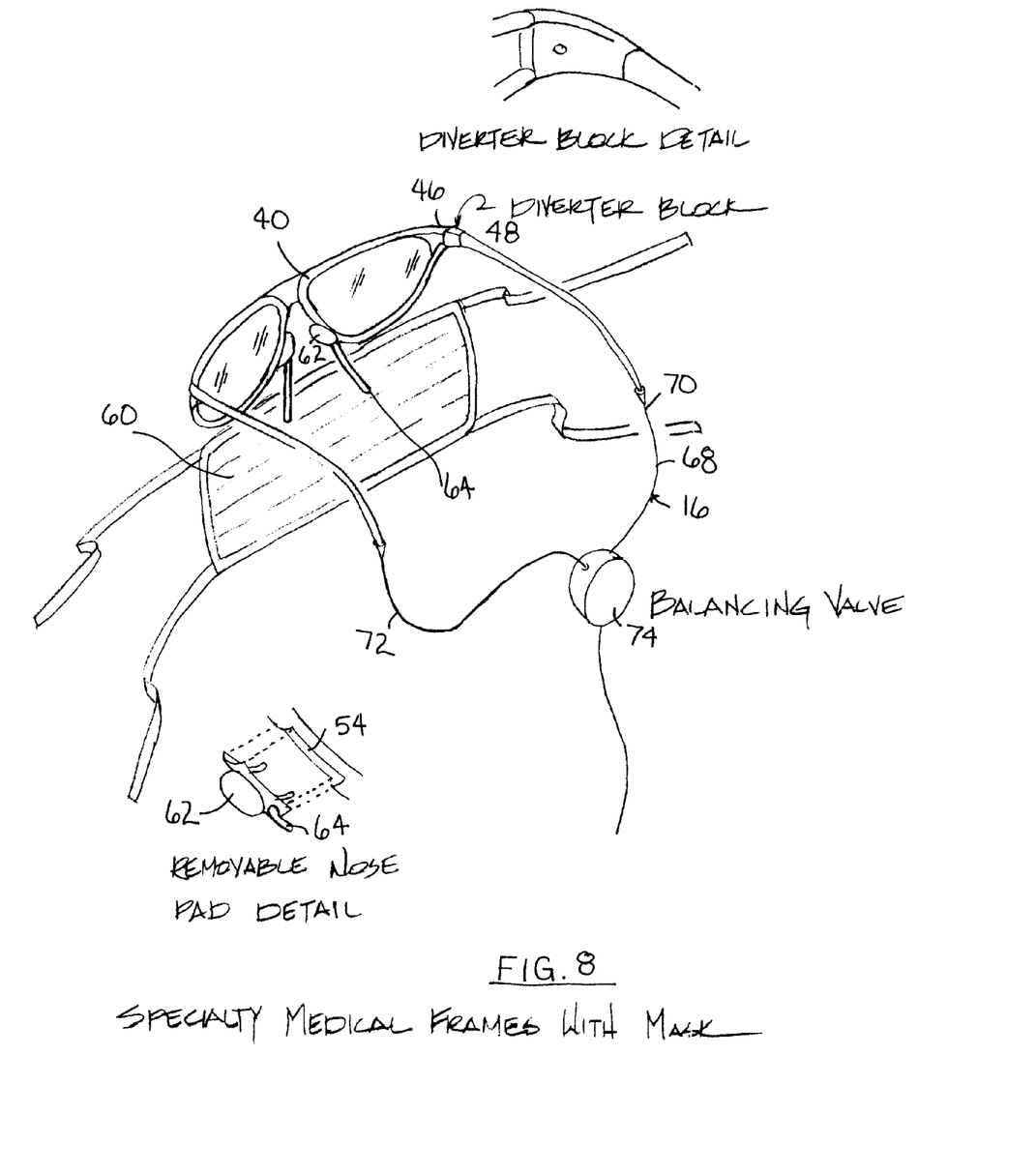
FIG. 8 is a perspective view of a glasses unit (i.e., specialty frames) including a cannula and a face mask in accordance with an embodiment of the invention.
Figure 9:
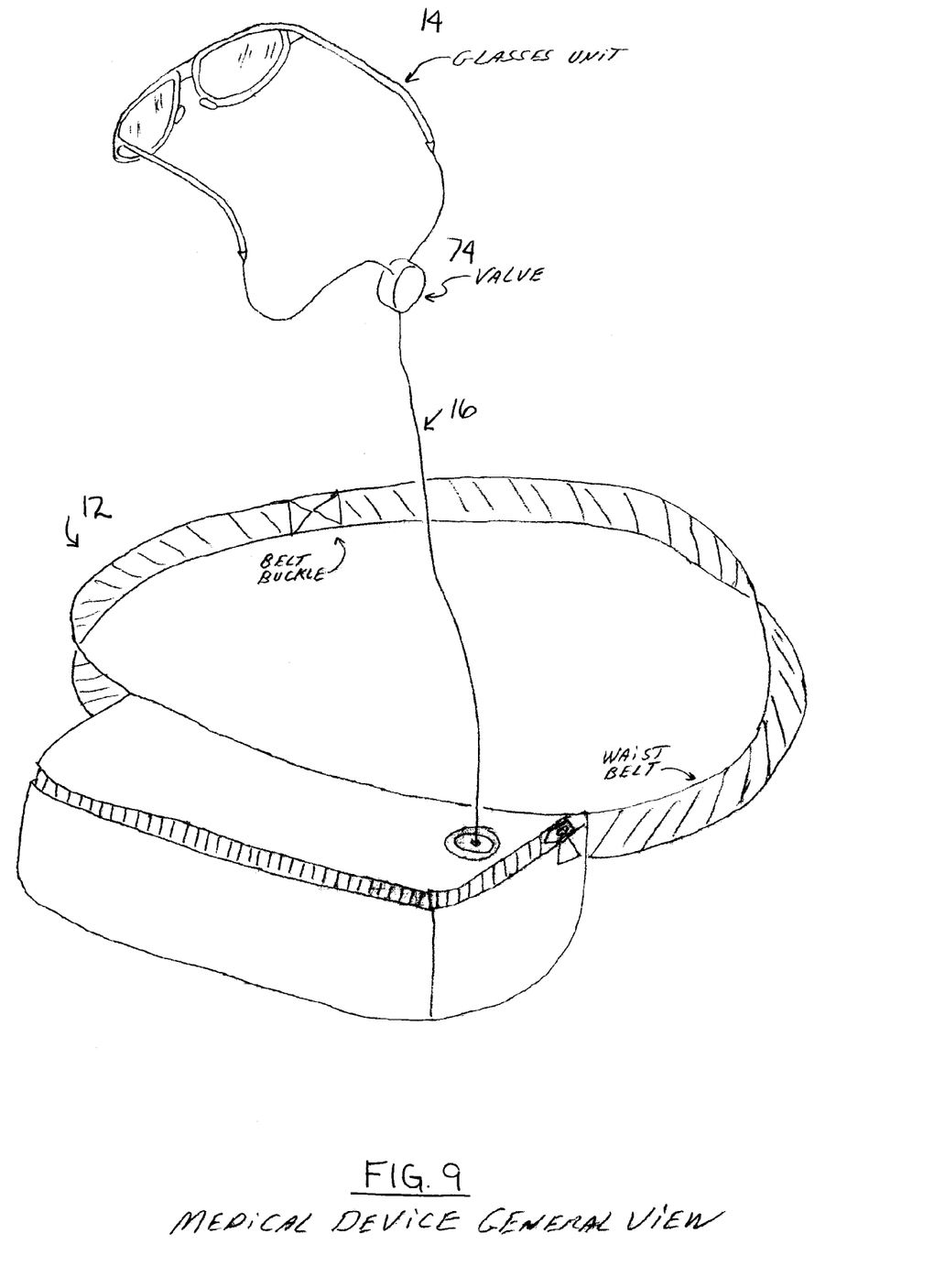
FIG. 9 is a perspective view of a medical device in accordance with an embodiment of the invention.

Referring now to the drawings wherein like reference numerals are used to identify identical components in the various views, FIG. 1 illustrates a flow chart for a medical device 10 shown in FIG. 9 in accordance with an embodiment of the invention. Medical device 10 may be provided for the treatment and prevention of eye and respiratory tract conditions, ailments, and diseases. Examples of such eye and respiratory tract conditions, ailments, and diseases include, but not limited to, dry eyes, environmental irritants, allergies from the environment, burns, smoke exposure and/or recovery from cataract surgery. Medical device 10 may be portable in an embodiment. For example, medical device 10 may be designed to create a portable clean room style environment. In one example and without limitation, this environment may be created around the eyes and respiratory tract to relieve eye and respiratory ailments. Medical device 10 may also be designed to create a portable humidity controlled environment. In one example and without limitation, this environment may be created around the eyes and respiratory tract. Medical device 10 may further be designed to create a portable drug delivery process to provide for extended and/or sustained exposure time to drug treatment regimens. In one example and without limitation, the medical device may be used to treat ailments of the eyes and respiratory tract. The size of the various components of medical device 10 may be configured for portability. However, the size of each component may vary depending upon the specific application (e.g., treatment) requirements of the medical device. Medical device 10 may also comprise a stationary platform in another embodiment. Medical device 10 may include a pack 12, a glasses unit 14, and a tube 16 (e.g., FIGS. 2-8). Although a glasses unit 14 is mentioned in detail other types of units for creating portable clean room style or humidity controlled environments or for delivering medications and/or drug treatments may be used. For example, and without limitation, pack 12 and tube 16 may be used in connection with a bubble-like enclosure taped over a wound or surrounding an arm or leg. Pack 12 and tube 16 may also be used in connection with open cell foam diffuser sheet underneath a bandage to aid healing of a wound. These and similar units may be used for applications where a portable, sterile actively circulating medicated and/or humidified air environment is desired on any part of a patient's body.

Figure 2:
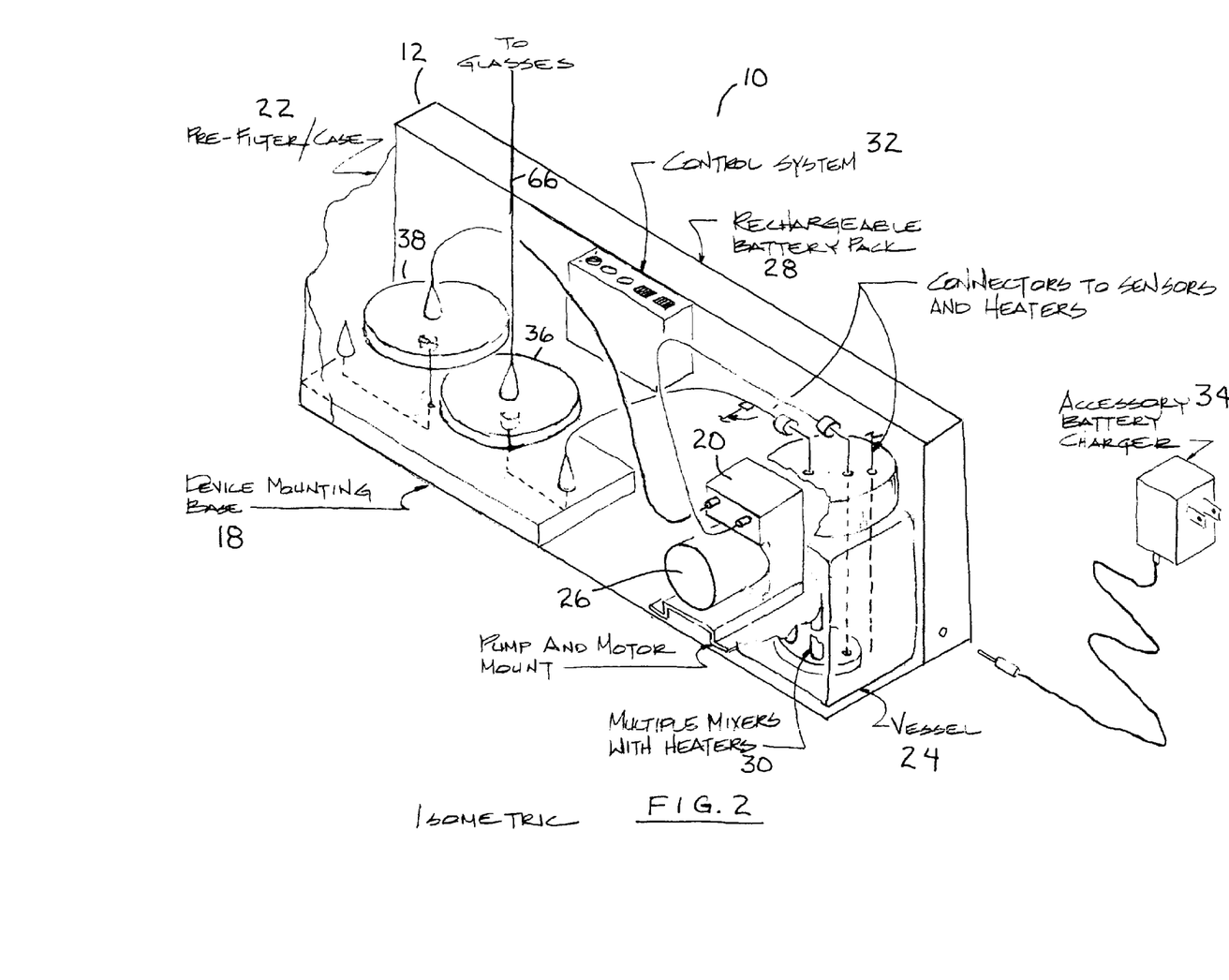
FIG. 2 is an isometric view of a pack for a medical device in accordance with an embodiment of the invention.

Referring now to FIG. 2, pack 12 may be provided for containing, housing, and/or carrying various components required in medical device 10 to treat and prevent eye and respiratory tract conditions, ailments, and diseases. These components may be used for filtration, humidification, and/or the delivery of various drug treatments. These components may be mounted on a base 18 within pack 12. Pack 12 may house or contain a pump 20, at least one filter 22, and a vaporizer chamber 24, for example. Pack 12 may be configured to look like any other accessory conventionally worn, so as not to provide attention to the medical need of a user. Pack 12 may include an integral, adjustable belt (not shown) to allow the user of the medical device to fit pack 12 comfortably on the body (e.g., around the waist). Pack 12 may comprise any number of materials, including for example, leather or synthetic cloth (e.g., polyester, DACRON™, or ballistic nylon). Pack 12 may have approximate dimensions of about 6"×3"×5". Although these approximate dimensions are mentioned in detail, pack 12 may have smaller or larger dimensions in other embodiments. For increased portability, it may be desirable to maintain dimensions equal to or less than about 6"×3"×5". The pack 12 may also be embodied in a shoulder purse or a back pack.

Pump 20 is provided for drawing in ambient air. Pack 12 may include a port (not shown) for air intake. Pump 20 may be configured to drive the ambient air and processed air through medical device 10. Pump 20 may utilize a motor 26 to provide the energy (i.e., motive energy) necessary to move the ambient air. Pump 20 may be configured to deliver a minimum of 1.5 standard liters of air at STP (i.e., standard temperature and pressure). Although 1.5 standard liters of air is mentioned in detail, pump 20 may be configured to deliver fewer or more liters of air in other embodiments. The motor of pump 20 may be operated, driven, and/or powered by a battery pack 28.

Battery pack 28 may comprise a rechargeable power source to provide the energy needed to operate the medical device. Battery pack 28 may comprise 2500 MaH NiMH batteries to drive the pump 20, heater 30, and control system 32 (as described in more detail below). Although this battery technology is mentioned in detail, battery pack 28 may utilize any number of technologies in other embodiments. NiMH may be preferred for its ability to deliver current nearest to its rated operating voltage for a period of time. Battery pack 28 may utilize 12 volts as the source of energy, but other voltages may be used to accommodate alternate battery technologies in various embodiments. In an embodiment, battery pack 28 may be configured to provide the energy needed to operate the medical device 10 (e.g., pump 20, heater 30, and control system 32) for at least four hours. Although four hours is mentioned in detail, battery pack 28 may be configured to operate the medical device for fewer or more hours in other embodiments. Battery pack 28 may also be configured for calibration adjustment. Medical device 10 may further comprise a battery charger (not shown). The battery charger may comprise an onboard electronic circuit to charge battery pack 28 from electrical energy provided from an accessory (e.g., plug-in) wall charger 34 or from a 13.4 volt auxiliary plug generally found in most automobiles. Plug-in wall charger 34 may supply the necessary voltage and current to the onboard battery charger. The onboard battery charger may be adapted or selected to transform any alternating current to the direct current utilized by the medical device 10 in an embodiment. The device 10 may also be powered directly from an external alternating current power source using an AC to DC direct current power supply.

Filter 22 may be provided for filtering air drawn in by pump 20. Filter 22 may filter dust and atmospheric particulates out of the air stream. Filter 22 may also filter environmental irritants and biological/viral hazards from the air stream. For example and without limitation, filter 22 may filter smog, soot, pollen, airborne allergens, dirt and sand blown into the air by wind gusts, bacteria (e.g., tuberculosis), and virus-containing aerosols generated by other people sneezing or coughing. Filter 22 may comprise one or more filters. The filters may be of different efficiencies to suit the user's needs. Furthermore, the filters may be ordered or placed in any number of various orders or configurations to suit the user's needs. In one embodiment, filter 22 may comprise a pre-filter. For example, the ambient air may be drawn through the pre-filter before introduction into vaporizer chamber 24. The pre-filter may be configured to remove atmospheric particulate to keep the device clear of contamination. For example, the pre-filter may have a minimum 95% efficiency using atmospheric dust. The pre-filter may comprise woven microfibers. The filter cartridge of the pre-filter may be configured to be readily replaceable by the user of the medical device 10.

In another embodiment, the filter may comprise a bacterial filter 38. For example, bacterial filter 38 may be used after the air passes through vaporizer chamber 24, in an embodiment. Bacterial 38 may also comprise woven microfibers (e.g., finer grade than pre-filter 22) or cellulose in an embodiment. The filter cartridge of the bacterial filter may be configured to be readily replaceable by the user of the medical device 10. Bacterial filter 38 may comprise a 0.22 micron rated bacterial filter. Although this particular rated bacterial filter is mentioned in detail, other bacterial filters, and filter materials may be used.

In another embodiment, the filter may comprise a specialty filter 36. Specialty filter 36 may be installed and/or utilized before or after air passes through vaporizer chamber 24, depending upon the effect that humidity may have on the specialty filter 36. The location of the specialty filter may be selected to avoid plugging up the specialty filter 36 with excess moisture in some instances. In other instances, the specialty filter 36 may work better with moisture. Specialty filter 36 may be a chemical filter and may be configured to remove atmospheric vapor hazards (e.g., acid vapor) from the medical device's process air stream. Specialty filter 36 may comprise activated charcoal in an embodiment. Activated charcoal may absorb chemical irritants in the ambient air.

While the filter of the medical device 10 has been described as one of a pre-filter 22, a specialty filter 36, or a bacterial filter 38, the medical device may use the combination of pre-filter 22, specialty filter 36, and bacterial filter 38, or any other combination thereof. Generally, the use of pre-filter 22 and bacterial filter 38 is recommended to maintain the cleanliness of the process air stream. However, pre-filter 22 or bacterial filter 38 or the combination thereof may be removed in some embodiments. Furthermore, while the pre-filter 22 is described as being configured for use before vaporizer chamber 24, the pre-filter 22 may be configured for use after vaporizer chamber 24 in other embodiments. Similarly, while the bacterial filter 38 is described as being configured for use after vaporizer chamber 24, the bacterial filter 38 may be configured for use before vaporizer chamber 24 in other embodiments. Specialty filter 36 may be removed in some embodiments.

Vaporizer chamber 24 may be provided for storing fluid and selectively supplying fluid vapor to the air drawn in by pump 20. In one embodiment, the fluid may be water to produce water vapor that may be supplied to incoming air in order to provide humidified air. In other embodiments, the fluid may be any other fluid to produce a desired vapor additive. For example, drugs or medication may be placed in vaporizer chamber 24 to allow exposure of the drug and/or medication to the eyes for various treatment options. Pack 12 may include a port for fluid, and a port for a drug additive stored in vaporizer chamber 24. Vaporizer chamber 24 may allow the processed air stream to serve as an eye medication delivery vehicle for substances capable of being evaporated into the processed air stream. Vaporizer chamber 24 may also allow the processed air stream to serve as a respiratory tract medication delivery vehicle for substances capable of being evaporated into the processed air stream. The air drawn in by pump 20 may be introduced into vaporizer chamber 24. Vaporizer chamber 24 may be configured to cause fluid/air interaction to selectively supply fluid vapor to the air drawn in by pump 20 up to the point of saturating the air with vapor. If humidity or drug treatments are not required under a particular application or treatment protocol, then vaporizer chamber 24 may be kept empty. Under this circumstance (i.e., where vaporizer chamber 24 is empty), device 10 may provide filtration only. Vaporizer chamber 24 may be configured to contain and/or store at least 4.5 ounces of fluid. Although this amount of fluid is mentioned in detail, vaporizer chamber 24 may be configured to store more or less than 4.5 ounces of fluid in other embodiments. Vaporizer chamber 24 may be capable of saturating about 1.5 standard liters of dry air per minute at an ambient temperature of 105° F. dry bulb and 2% relative humidity. Again, although this capability of vaporizer chamber 24 is mentioned in detail, vaporizer chamber 24 may be capable of saturating more or less air under different circumstances in other embodiments.

Vaporizer chamber 24 may include a heater 30 in some embodiments. Heater 30 may be configured for heating fluid stored in vaporizer chamber 24 above ambient temperature. Heater 30 may thus be used to aid evaporation. Heater 30 may be configured to heat fluid stored in vaporizer chamber 24 to a temperature differential of about 50° F. Although 50° F. is mentioned in detail, heater 30 may be configured to heat fluid to more or less than this temperature differential in other embodiments. The higher temperature fluid may be supplied to the air, up to the saturation point, and then delivered to the eye area of the user of device 10. Heater 30 may be used to keep the vaporizer chamber 24 from freezing under certain conditions (e.g., if the device 10 was kept in a cold environment for an extended period of time). Medical device 10 may be configured to automatically turn on heater 30 if the temperature of the fluid in the vaporizer chamber 24 reaches a set and/or predetermined lower threshold. Heater 30 may also be configured for maintaining a predetermined temperature of the fluid stored in vaporizer chamber 24. Heater 30 may also be used to maintain and/or control the temperature of the vaporizer chamber 24 so that it does not exceed approximately 10-20 degrees over ambient temperature, but not over 105° F. While 105° F. is mentioned in detail as a threshold to prevent unsafe conditions around the eyes, heater 30 may be configured to maintain and/or control the temperature of vaporizer chamber 24 so that it does not exceed a higher or lower temperature in other embodiments. Vaporizer chamber 24 may include a vaporizer chamber temperature sensor (not shown). Medical device 10 may also include an ambient temperature sensor (not shown) in some embodiments. The vaporizer chamber temperature sensor and the ambient temperature sensor may be used in maintaining and/or controlling the temperature of vaporizer chamber 24 to maintain a certain and/or predetermined temperature. These sensors may be configured for calibration adjustment.

The controlled temperature of vaporizer chamber 24 (e.g., maintaining the temperature of the fluid within the vaporizer chamber 24 within approximately 10-20 degrees of ambient temperature) may prevent and/or lessen condensation following delivery of the air and/or vapor from the vaporizer chamber 24. In another embodiment, the desired effect of the treatment protocol or regimen may require and/or prefer that the vapor condense and/or fog at or around the eye area following delivery of the vapor. In this embodiment, the temperature of vaporizer chamber 24 may be maintained and/or controlled so that the air and vapor coming out of the diffuser may be saturated and/or heated so that it will condense and/or fog as it cools to ambient temperature at or around the eye area of the user of device 10. Accordingly, device 10 may be programmed to avoid condensation/fogging in some embodiments or may be programmed to ensure condensation/fogging following delivery of the air and/or vapor to the eye area in other embodiments in order to meet the requirements of the designated application or treatment protocol.

Medical device 10 may include an interface (e.g., software and connecting cable) to allow medical personnel or other individuals to designate or set user adjustable parameters in the medical device. For example, medical device 10 may be set with a vaporizer chamber temperature set point that will be used to control the temperature of vaporizer chamber 24. Medical device 10 may also be set with the preferred temperature differential set point between the ambient temperature and the vaporizer chamber temperature. As described above, the temperature differential set point between the sensed temperature of the ambient temperature sensor and the sensed temperature of the vaporizer chamber temperature sensor may control whether the delivered air and/or vapor will eventually create fog or condensation at some point after delivery.

Figure 3:
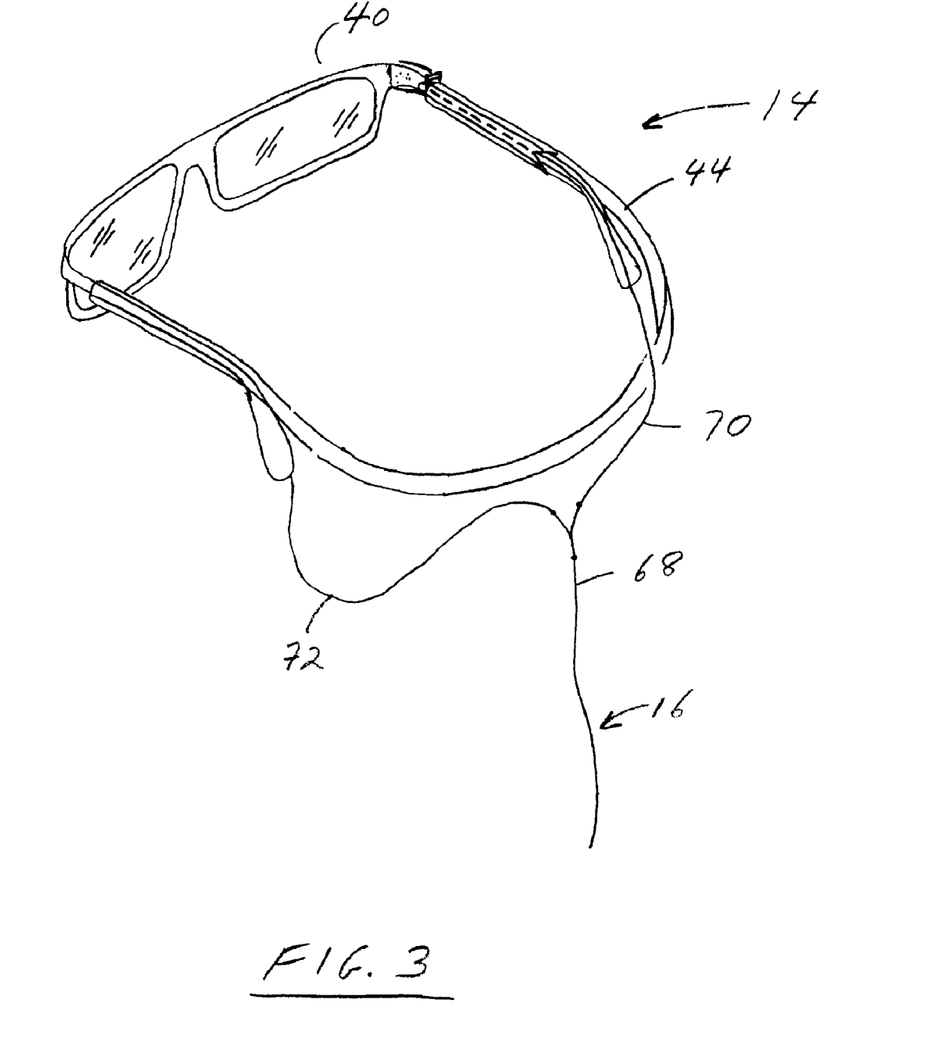
FIG. 3 is a perspective view of a glasses unit (i.e., adapted commercially available frames) in accordance with an embodiment of the invention.
Figure 4:
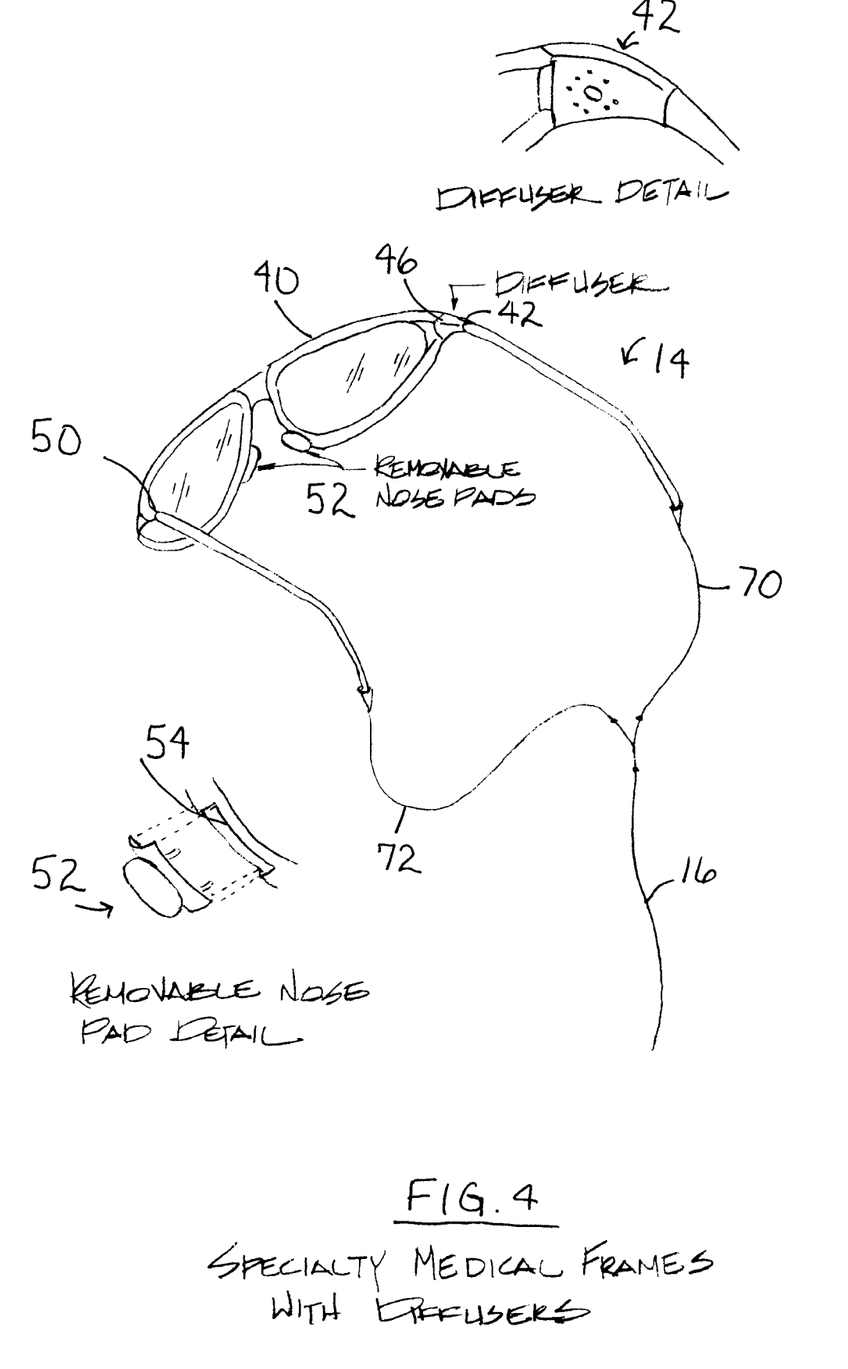
FIG. 4 is a perspective view of a glasses unit (i.e., specialty frames) in accordance with an embodiment of the invention.

Referring now to FIGS. 3-4, medical device 10 may further include glasses unit 14. Glasses unit 14 may be provided for fitting over both of the eyes of a user of medical device 10. Glasses unit 14 may be configured to be separated from pack 12 when device 10 is in use. Glasses unit 14 may include frames 40 and diffuser 42.

Frames 40 may be provided to allow convenient access to the eye area of a user of medical device 10. Frames 40 may comprise a pair of spectacle-like frames. The glass of frame 40 may be tinted or not, polarized or not, off the shelf, prescription or not, or any combination thereof. In some embodiments, frames 40 may not fully enclose the eye area of a user of medical device 10. Frames 40 may minimize the open area between frames 40 and a user's face in some embodiments, although no effort may be made to create a positive seal between the user's face and the glasses unit 14. While not preferred, medical device 10 may utilize a positive seal between the user's face and the glasses unit 14 in other embodiments. In an embodiment illustrated in FIGS. 3 and 5, frames 40 may comprise a pair of conventional, commercially available frames. Frames 40 may be attached to an adaptor 44 to allow frames 40 to be used as part of medical device 10. In particular, frames 40 may have stems that are capable of sliding into the adaptor 44 containing feed tube 16. Feed tube 16 may be configured for connection or attachment to a diffuser 42. The diffuser 42 shown in FIG. 3 may comprise a clip-on diffuser and may be configured to be clipped on or otherwise connected to frames 40.

Figure 7:
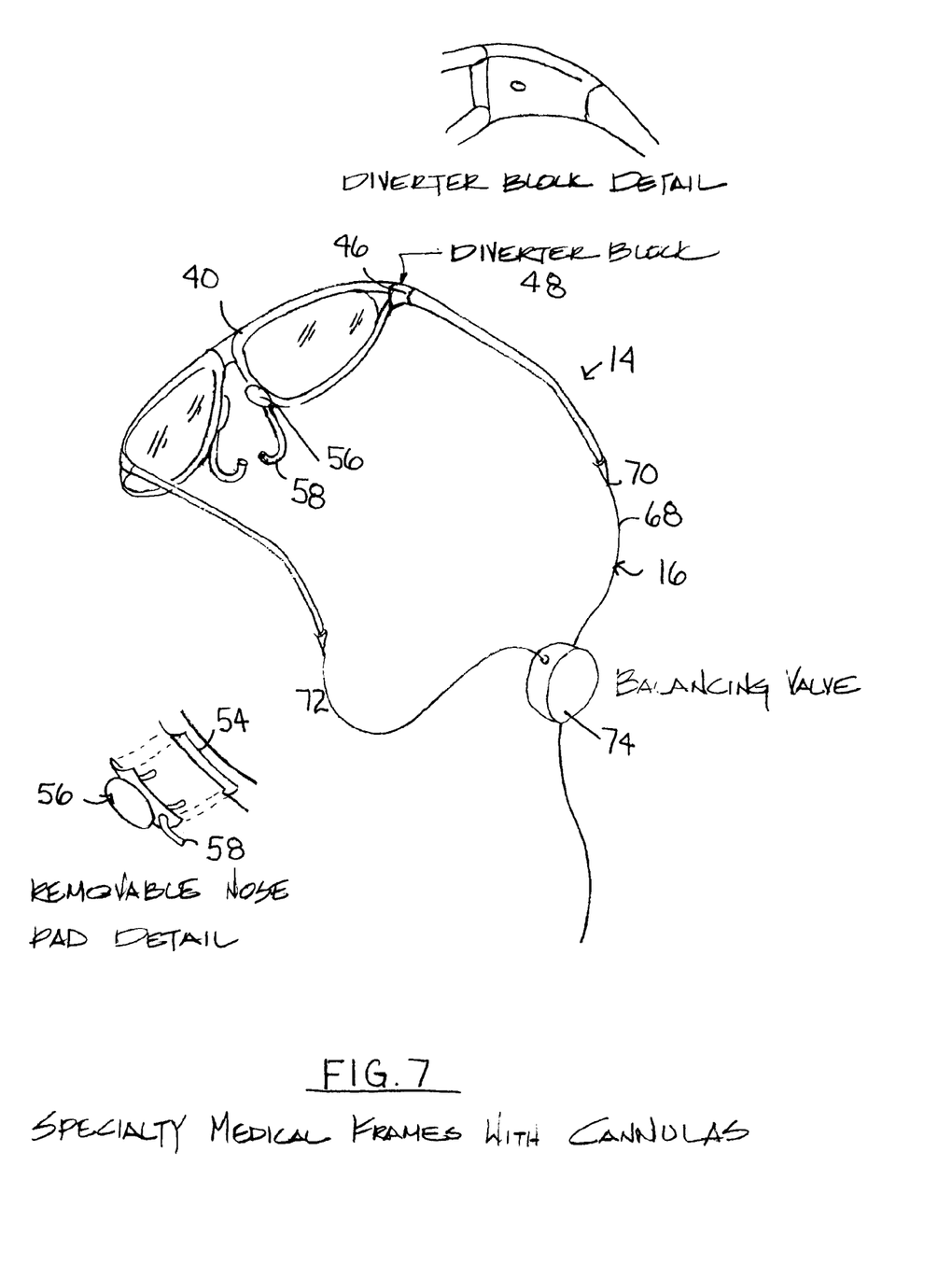
FIG. 7 is a perspective view of a glasses unit (i.e., specialty frames) including a cannula in accordance with an embodiment of the invention.

In another embodiment illustrated in FIG. 4, frames 40 may comprise a pair of specialized frames specifically adapted for use with medical device 10. For example, frames 40 may comprise openings 46 to receive diffuser 42. In an embodiment, openings 46 may be located at the upper outside corners of frames 40. Referring now to FIG. 7, in some embodiments, a diffuser 42 may not be required. In these embodiments, a blank plug 48 (e.g., diverter block) may be used to plug opening 46 when a diffuser 42 is not necessary for the application (e.g., treatment) and has been removed from frames 40. Referring again to FIG. 4, the diffuser 42 may be placed into and used in opening 46 when a diffuser is necessary for an application (e.g., treatment). Accordingly, diffuser 42 may be removably connected to frames 40 in an embodiment in order to suit the particular application with which the medical device is to be used.

Diffuser 42 may be provided to deliver air drawn in from pump 20 following the filtration and/or selective supply of fluid vapor to the air. For example, diffuser 42 may be provided to introduce air into the eye chamber of frames 40 in a desired pattern and at a desired velocity. The diffuser 42 of device 10 may also be used to introduce filtered air, humidity, and/or drag treatments to the respiratory tract by using the air exiting the glasses unit 14 to create a boundary layer of treated air on the face to be introduced around and across the nose and mouth, in addition to around the eye area of the user. Glasses unit 14 may comprise a first and second diffuser 42, 50. First diffuser 42 may be proximal a first eye of a user, and second diffuser 50 may be proximal a second eye of a user. Both the first and second diffusers 42, 50 may be used to deliver air drawn in from pump 20 following the filtration and/or selective supply of fluid vapor to the air. Diffusers 42, 50 may contain any number of perforations to either increase or decrease the flow of air as required or preferred for a particular treatment. Diffusers 42, 50 may have the same or a different number of perforations depending on the treatment. The air delivered by diffuser 42, 50 may not include any liquid at the time of delivery by diffuser 42, 50. For example, the air delivered by diffuser 42, 50 may not include liquid droplets, in either aerosol or mist form, at the time of delivery. The absence of liquid droplets, in either aerosol or mist form, allows for improved control of moisture in the eye cavity, thereby making the diffuser less vulnerable to ambient conditions. Diffuser 42, 50 may comprise an aspirating or a non-aspirating diffuser, depending upon the medical need of a user of device 10. An aspirating diffuser may generally mix incoming air with air already in the eye chamber via high velocity aspirating air streams. For example, an aspirating diffuser may utilize a directed nozzle. Aspirating diffusers may be designed to directed the process air stream to a specific point within the eye chamber. On the other hand, a non-aspirating diffuser may distribute air perpendicular to the face of the diffuser and may not generally cause aspiration or mixing of air due to high-velocity jets. Non-aspirating diffusers may be designed to introduce the process air stream into the eye chamber in a low velocity way that does not generate multiple counter currents. Non-aspirating diffusers may also be designed to avoid generating a perceptible air current across the surface of the eyes. The diffuser 42, 50 may be designed to gently introduce air into the eye chamber of frames 40 to create a conditioned environment for the surface of the eyeball of a user of device 10. Following delivery, the air and fluid provided by diffuser 42, 50 may cool down and may cause condensation. However, the controlled temperature of the vaporizer chamber 24 may prevent and/or lessen condensation of the vapor.

Figure 6:
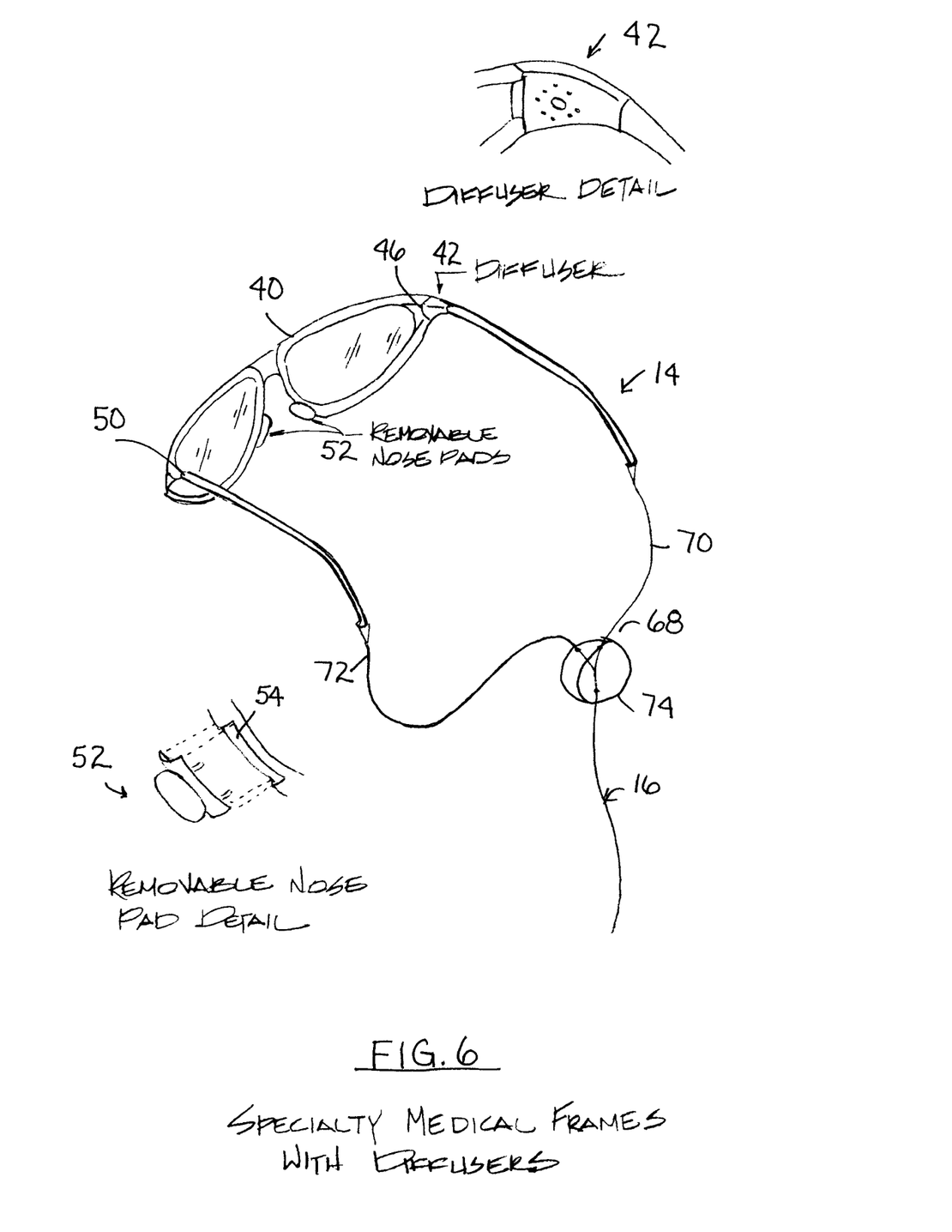
FIG. 6 is a perspective view of a glasses unit (i.e., specialty frames) including a valve in accordance with an embodiment of the invention.

Referring now to FIGS. 4 and 6, in an embodiment, glasses unit 14 may further comprise a nose pad 52. Glasses unit 14 may include one or more nose pads 52 in an embodiment. Nose pad 52 may be configured to support the glasses unit 14 on the bridge of the nose when medical device 10 is in use. In connection with the specialized frames, the frames 40 may contain two openings 54 that are normally concealed under the nose pads 52. Nose pads 52 may be removable from frames 40. Nose pad 52 may be removable to allow for the insertion of alternate nose pads as described in detail below.

Various type of nose pads may be configured for use with glasses unit 14 when glasses unit 14 comprises a pair of specialized frames specifically adapted for use with medical device 10. For example, a first type of nose pad 52 may not include any other structure and may be used only to plug and/or block openings 54 in the specialized frames.

Referring now to FIGS. 7-8, in some embodiments, more positive introduction of the treated air into the nose may be required. In these embodiments, the tube 16 may be routed directly into the nose. For example, the supply tube 16 may be routed through frames 40 as shown in FIG. 7, and a second type of nose pad 56 may include a cannula 58. The cannula 58 may be configured for insertion into the nose of a user of medical device 10. Cannula 58 may be provided so that the medical device 10 may filter dust, environmental irritants, and biological/viral hazards from air delivered to the eye area of a user (e.g., the eye cavity behind glasses unit 14) and the nose area for delivery to the lungs. Although FIG. 7 illustrates the use of cannula 58 with a blank plug 48 in place of diffuser 42 in frames 40, the frames 40 may utilize both a diffuser 42 and a cannula 58 in other embodiments, depending upon the treatment that is required or preferred.

Referring now to FIG. 8, medical device 10 may further comprise a mask 60 configured to form an enclosure around the eye, nose, and/or mouth area of a user of medical device 10. Mask 60 may comprise a standard, conventionally available mask used to protect the respiratory tract from environmental airborne hazards. A third type of nose pad 62 may include a cannula 64 configured for insertion into an enclosure formed by the medical mask 60. Cannula 64 may extend generally more straight than the curved cannula depicted in FIG. 7 and configured for insertion into the nose of a user of device 10. Again, cannula 64 may be provided so that the medical device 10 may filter dust, environmental irritants, and biological/viral hazards from air delivered to the eye area of a user (e.g., the eye cavity behind glasses unit 14) and the nose and mouth area for delivery to the lungs. Although FIG.

8 illustrates the use of cannula 64 with a blank plug 48 in place of diffuser 42 in frames 40, the frames 40 may utilize both a diffuser 42 and a cannula 64 in other embodiments, depending upon the treatment that is required or preferred. The various types of nose pads 52, 56, 62 may all be utilized on a single glasses unit 14 depending upon the need of the user of device 10.

Medical device 10 may further include tube 16 for delivering and/or supplying air, vapor, and/or drug treatments from pack 12 to glasses unit 14. Tube 16 may comprise medical grade tubing and may comprise polypropylene, polyvinyl chloride (PVC), or high density polyethylene (HDPE) in some embodiments. Although these materials are mentioned in detail, tube 16 may comprise any other number of materials. Tube 16 may have generally thin walls in some embodiments, but may be of at least sufficient thickness to prevent collapse and/or pinching of tube 16 under normal portable movement of the user of device 10. The dimensions of tube 16 may vary in accordance with the treatment protocols or regimens for which medical device 10 may be used. However, tube 16 may be of sufficient length to allow for separation of pack 12 from glasses unit 14 on any number of individuals of varying sizes. Tube 16 may also include one or more loops (not shown) to allow for expansion of tube 16 as necessary to accommodate various sizes and human movement (e.g., bending and twisting). Tube 16 may also have an inside diameter of about 0.250 inches or less in some embodiments. Although this inside diameter is mentioned in detail, the inside diameter of tube 16 may be larger or smaller in other embodiments. Tube 16 may have a first end 66 (e.g., FIGS. 1-2) and a second end 68 (e.g., FIGS. 3-8). Referring now to FIGS. 1-2, first end 66 may be configured for connection to pack 12. Referring now to FIGS. 3-8, second end 68 may be configured for connection to diffuser 42 on glasses unit 14. In the embodiment with more than one diffuser, second end 68 of tube 16 may include a first and second supply hose 70, 72. First supply hose 70 may be connected to first diffuser 42, and second supply hose 72 may be connected to second diffuser 50. Accordingly, tube 16 may supply the air, vapor, and/or drug treatments into either side of the frames 40 of glasses unit 14. Tube 16 may further extend through frames 40 toward cannula 58, 64 in order to supply the air, vapor, and/or drug treatments to the cannula 58, 64 where required (e.g., as shown in FIGS. 7-8). When diverter blocks 48 are used in place of diffusers 42, 50 as illustrated in FIGS. 7-8, first supply hose 70 may extend through frames 40 and be configured for connection to cannula 58, 64, and second supply hose 72 may also extend through frames 40 and be configured for connection to cannula 58, 64. The frames 40 may be hollow to allow the process air to flow through the frames 40 to the cannula 58, 64.

Referring now to FIGS. 5-8, device 10 may further include a valve 74 disposed along tube 16. Valve 74 may be disposed at the location along tube 16 where tube 16 splits into first and second supply hoses 70, 72. Valve 74 may be provided for controlling the amount of air supplied to first and second supply hose 70, 72, respectively. Accordingly, valve 74 may be configured to control the amount of air supplied to each side of frames 40, and therefore, to each eye of a user. For example, valve 74 may be configured to allow medical personnel to divert the optimal percentage of air between the two eyes. Valve 74 may also be configured to divert the optimal percentage of air between either nostril. Valve 74 may thus allow delivery of different percentages of the total process air stream to each eye and/or nostril. Valve 74 may comprise medical grade plastic in an embodiment. For example and without limitation, valve 74 may comprise polypropylene, PVC, or HDPE. Although these materials are mentioned in detail, any number of other materials may be used. Valve 74 may have an inside diameter configured to match the inside diameter of tube 16. For example, valve 74 may have an inside diameter of about 0.250 inches or less in some embodiments. Although this inside diameter is mentioned in detail, the inside diameter of valve 74 may be larger or smaller in other embodiments.

Device 10 may further include a control system 32 in an embodiment. Referring now to FIG. 1, for example, control system may include both a light display and an audible alarm. Control system 32 may be configured to turn on and off medical device 10. Control system 32 may also be configured to provide information regarding the strength of battery pack 28. For example, control system 32 may be configured to provide a visual or audible indication of the strength of battery pack 28. Accordingly, medical device 10 may include a battery pack sensor (not shown). Control system 32 may also be configured to provide information regarding the level of fluid in vaporizer chamber 24 (e.g., a visual or audible indication of the level of fluid in vaporizer chamber 24). Accordingly, medical device 10 may include a vaporizer chamber fluid volume sensor (not shown). In another example, control system 32 may be configured to provide information regarding the flow of fluid from vaporizer chamber 24 (e.g., a visual or audible indication of the flow of fluid from vaporizer chamber 24). Accordingly, medical device 10 may include a vaporizer chamber low fluid volume sensor (not shown). Medical device 10 may also include a high pressure, a low pressure switch, or a high pressure and low pressure switch. A high pressure may indicate that the path of fluid flow is blocked. In an embodiment, if the battery pack sensor indicates that battery voltage has reached a threshold level, the low battery and/or low flow alarm may be automatically turned off to conserve energy. The threshold level may be set and/or predetermined by the user, medical personnel, or another individual.

Control system 32 may also be configured to provide information regarding the temperature of fluid in vaporizer chamber 24. For example, control system 32 may be configured to provide a visual or audible indication of the temperature of fluid stored in vaporizer chamber 24. In one embodiment, control system 32 may produce a visual or audible alarm if the temperature of the fluid in vaporizer chamber 24 goes below a low threshold level. For example, control system 32 may produce a visual or audible alarm if the temperature of the fluid in vaporizer chamber 24 goes below 36° F. toward 32° F. and freezing. Although 36° F. is mentioned in detail, control system 32 may produce a visual or audible alarm if the temperature of the fluid in vaporizer chamber 24 goes below a higher or lower threshold level in other embodiments. In another embodiment, control system 32 may produce a visual or audible alarm if the temperature of the fluid in vaporizer chamber 24 goes above a high threshold level. For example, control system 32 may produce a visual or audible alarm if the temperature of the fluid in vaporizer chamber 24 goes above 95° F. Although 95° F. is mentioned in detail, control system 32 may produce a visual or audible alarm if the temperature of the fluid in vaporizer chamber 24 goes above a higher or lower threshold level in other embodiments. In addition, medical device 10 may be configured to automatically disable heater 30 if the high threshold level is met. A user, medical personnel, and/or other individuals may set and/or adjust the low and high threshold levels (e.g., vaporizer chamber temperature alarm set points) in accordance with a desired and/or predetermined level.

Control system 32 may be configured to receive user input and acknowledgement (e.g., acknowledgment of various alarm conditions). An acknowledgement button (not shown) may be used on medical device 10 to allow a user of the medical device to silence and/or turn off an alarm (e.g., a visual or audible indication). Medical device 10 may further include a miniature LCD message display panel. In accordance with an embodiment of the invention, the LCD display panel may be configured to display at least twelve 0.25 inch characters. A conventional microprocessor device controller may contain program software as is known to one of ordinary skill in the art to manage the inputs and outputs for medical device 10 as described herein.

Methods of treating and preventing eye and respiratory tract conditions utilizing medical device 10 are also disclosed herein. A method of treating and preventing eye and respiratory tract conditions may comprise the step of providing a medical device 10. Medical device 10 may comprise a pack 12. Pack 12 may comprise a pump 20 for drawing in ambient air, at least one filter 16, 36, 38 for filtering air drawn in by pump 20; and a vaporizer chamber 24 for storing fluid and selectively supplying fluid vapor to air drawn in by pump 20. The medical device may further comprise a glasses unit 14. Glasses unit 14 may be configured for fitting over both of the eyes of a user of device 10 and may be separated from pack 12 when medical device 10 is in use. Glasses unit 14 may comprise spectacle-like frames 40. Frames 40 may comprise a diffuser 42 connected to frames 40. The medical device may further comprise a tube 16. Tube 16 may have a first end 66 configured for connection to pack 12 and a second end 68 configured for connection to diffuser 42. The method of treating eye and respiratory tract conditions may further comprise the steps of filtering air drawn in from pump 20 in filter 16, 36, or 38 and delivering the filtered air to the eye area of the user. The filtered air may not include liquid at the time of delivery.

In some embodiments, the method of treating and preventing eye and respiratory tract conditions may further include supplying vapor or medication to the eye area or respiratory tract of a user. For example, in one embodiment, the method of treating eye and respiratory tract conditions may further include the steps of supplying vapor to the air drawn in from pump 20 and delivering the processed air to the eye area of the user. The air may not include liquid at the time of delivery.

In some embodiments, more direct treatment of the respiratory tract may be required. The methods may further include the steps of connecting a cannula 58, 64 to medical device 10 and delivering the filtered air to the cannula 58, 64. The methods may further include the steps of connecting to medical device 10 a mask 60 configured to form an enclosure around the nose area of the user of device 10 and delivering the filtered air to the enclosure. Depending upon the preferred treatment, diffusers 42, 50 may be removed from frames 40 and a block 48 may be configured to plug frames 40 in place of diffusers 42, 50 when cannula 58, 64 is connected to medical device 10.

These methods may further include the steps of supplying vapor to the air drawn in from pump 20 and delivering the air to cannula 58, 64 connected to the nose pad, 56, 62, respectively, of device 10. Cannula 56 may be configured for insertion into the nose of a user of device 10. Cannula 62 may be configured to deliver the air to the enclosure created by mask 60 that may also be connected to medical device 10.

The method of treating eye and respiratory tract conditions may further include introducing and delivering a medication to the eye area or respiratory tract of a user. In particular, the method of treating eye and respiratory tract conditions may further include the steps of introducing a medication into vaporizer chamber 24 and delivering the medication to the eye area of the user of device 10 by vaporization. The delivered medication may not include liquid at the time of delivery. In another embodiment, the method of treating eye and respiratory tract conditions may further comprise the steps of introducing a medication into vaporizer chamber 24 and delivering the medication to the cannula 58, 64 connected to the nose pad 52, 62 of device 10. In yet another embodiment, the method of treating eye and respiratory tract conditions may further comprise introducing medication into vaporizer chamber 24 and delivering the medication to the enclosure created by the mask 60 connected to the device 10.

Figure 10:
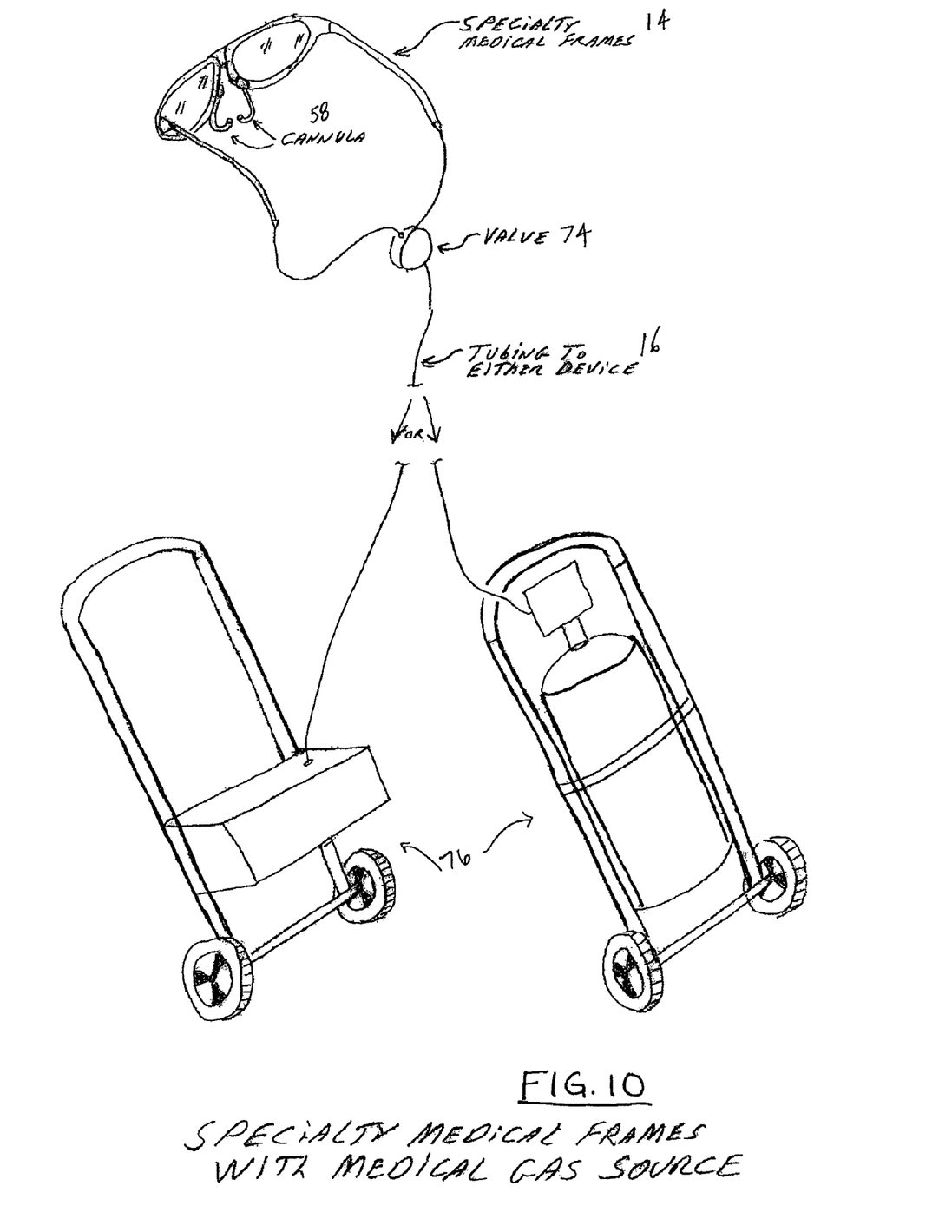
FIG. 10 is a perspective view of a medical device with portable medical gas sources in accordance with an embodiment of the invention.

Referring now to FIG. 10, another method of treating and preventing eye and respiratory tract conditions may comprise the step of providing a medical device similar to the embodiments described above in that it may include a glasses unit 14 and a tube 16. The glasses unit 14 may be configured to fit over both of the eyes of a user and may include spectacle-like frames 40, a diffuser 42, and a cannula 58. In an embodiment, the cannula 58 may be configured for insertion into the nose of a user of the medical device. The cannula may also be configured for insertion into an enclosure formed by connection of a medical mask to the glasses unit in another embodiment. In an embodiment, the cannula 58 may be configured for connection to glasses unit 14 through connection of the cannula 58 to a nose pad 56 of glasses unit 14. The tube 16 of the medical device 10 may have a first end 66 configured for connection (e.g., direct or indirect connection) to the glasses unit 14. The second end 68 of the tube 16 may be configured for connection to a container 76 for medical gas. The medical gas may comprise a bottled or otherwise generated medical gas. For example and without limitation, the medical gas may comprise oxygen. Although oxygen is mentioned in detail, the medical gas may comprise any of various medical gases supplied via compressed gas bottle or a molecular sieve or other device. The method may further include the steps of connecting the second end 68 of the tube 16 to the container 76 for medical gas and delivering the medical gas to the glasses unit 14. From the glasses unit 14, the medical gas may be delivered to the eyes and/or the respiratory tract. For example, the tube 16, diffuser 42, and/or cannula 58 may be utilized to deliver the medical gas to the eyes and/or the respiratory tract of the user of medical device 10. Cannula 58 may thus allow for more direct and discreet supply of medical gas (e.g., oxygen) delivery to patients from currently used tank supply systems (e.g., oxygen tank supply systems).

Figure 5:
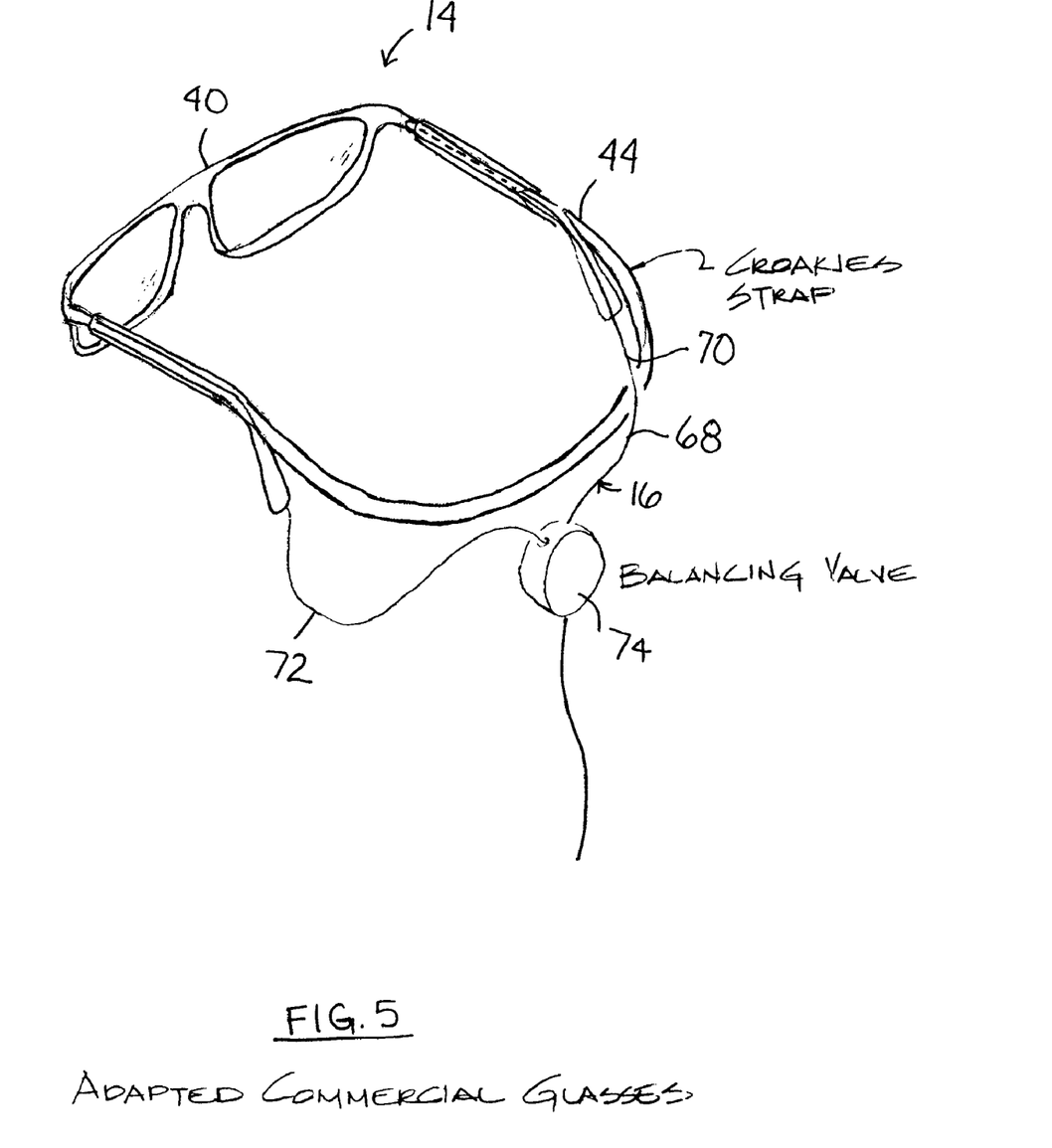
FIG. 5 is a perspective view of a glasses unit (i.e., adapted commercially available frames) including a valve in accordance with an embodiment of the invention.

A method of modifying a pair of glasses is also disclosed. The method of modifying a pair of glasses may be used to form a medical device 10 useful for treating eye and respiratory tract conditions. The glasses that may be modified may comprise any conventional, commercially available pair of frames 40 (e.g., as shown in FIGS. 3 and 5). The method of modifying a pair of glasses may include the step of providing a pack 12. The pack may include a pump 20 for drawing in ambient air, a filter 22, 36, and/or 38 for filtering air drawn in by pump 20, and a vaporizer chamber 24 for storing fluid and selectively supplying fluid vapor to air drawn in by pump 20. Pack 12 may be separated from the pair of glasses. The method of modifying a pair of glasses may also include the step of providing a tube 16 and connecting tube 16 to the glasses. Tube 16 may have a first end 66 configured for connection to pack 12 and a second end 68 configured for connection to a diffuser. The diffuser may be configured to deliver air drawn in from pump 20. The air may not include liquid at the time of delivery.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device for the treatment and prevention of eye and respiratory tract conditions comprising:
   a pack comprising:
      a pump for drawing in ambient air;
      a filter for filtering air drawn in by said pump;
      a vaporizer chamber for storing fluid and selectively supplying fluid vapor to air drawn in by said pump; and
   a glasses unit for fitting over both of the eyes of a user, said glasses unit comprising:
      spectacle-like frames;
      a first diffuser connected to said frames, said diffuser configured to deliver air drawn in from said pump, wherein said air does not include liquid at the time of delivery; and
      a removable nose pad;
   a tube having a first end and a second end, said first end of said tube configured for connection to said pack and said second end of said tube configured for connection to said diffuser; and
   a mask configured to form an enclosure around the nose area,
   wherein said glasses unit is separated from said pack when said medical device is in use, and
   wherein said nose pad includes a cannula configured for insertion into said enclosure of said mask.

2. The medical device of claim 1, wherein said diffuser is removably connected to said frames.

3. The medical device of claim 2, further comprising a block configured to plug said frames when said diffuser is removed from said frames.

4. The medical device of claim 1, wherein said device is portable.

5. The medical device of claim 1, wherein said pump is operated by a battery pack.

6. The medical device of claim 1, further comprising a system for providing a visual indication or audible indication of the level of fluid in said vaporizer chamber or the flow of fluid from said vaporizer chamber.

7. The medical device of claim 1, further comprising a second diffuser, wherein said first diffuser is proximal a first eye of a user and said second diffuser is proximal a second eye of said user.

8. The medical device of claim 7, wherein said second end of said tube comprises a first supply hose connected to said first diffuser and a second supply hose connected to said second diffuser.

9. The medical device of claim 1, further comprising a valve for controlling the amount of air supplied to each side of said frames.

10. The medical device of claim 1, further comprising a heater for said vaporizer chamber, said heater configured for heating said fluid above ambient temperature or maintaining a predetermined temperature of said fluid.

11. The medical device of claim 1, further comprising a system for providing a visual indication or audible indication of the temperature of said vaporizer chamber.

12. A method of treating eye and respiratory tract conditions, comprising:
   providing a medical device comprising:
      a pack comprising:
         a pump for drawing in ambient air;
         a filter for filtering air drawn in by said pump;
         a vaporizer chamber for storing fluid; and selectively supplying fluid vapor to air drawn in by said pump; and
      a glasses unit for fitting over both of the eyes of a user, wherein said glasses unit is separated from said pack when said medical device is in use, said glasses unit comprising:
         spectacle-like frames;
         a first diffuser connected to said frames, said diffuser configured to deliver air drawn in from said pump; and
         a removable nose pad; and
      a tube having a first end and a second end, said first end of said tube configured for connection to said pack and said second end of said tube configured for connection to said diffuser; and
      a mask configured to form an enclosure around the nose area, wherein said nose pad includes a cannula configured for insertion into said enclosure of said mask;
   filtering air drawn in from said pump in said filter;
   delivering the filtered air to the eye area of the user, wherein the filtered air does not include liquid at the time of delivery, and
   delivering the filtered air to the cannula and said enclosure of said mask.

13. The method of claim 12, further comprising:
   supplying vapor to the air drawn in from said pump; and
   delivering the air to the eye area of the user.

14. The method of claim 12, further comprising:
   supplying vapor to the air drawn in from said pump; and
   delivering the air to the cannula.

15. The method of claim 12, further comprising:
   introducing a medication into said vaporizer chamber; and
   delivering said medication to the eye area of the user by vaporization.

16. The method of claim 12, further comprising:
   introducing a medication into said vaporizer chamber; and
   delivering said medication to the cannula by vaporization.

17. A method of treating eye and respiratory tract conditions, comprising:
   providing a medical device comprising:
      a glasses unit for fitting over both of the eyes of a user, said glasses unit comprising:
         spectacle-like frames;
         a first diffuser connected to said frames;
         a removable nose pad;
         a mask configured to form an enclosure around the nose area; and
         a cannula connected to said removable nose pad, said cannula configured for insertion into said enclosure of said mask; and
      a tube having a first end and a second end, said first end of said tube configured for connection to said glasses unit;
   connecting said second end of said tube to a container for medical gas;
   delivering the medical gas to said glasses unit.

* * * * *